United States Patent
Faber et al.

(10) Patent No.: US 10,449,248 B2
(45) Date of Patent: Oct. 22, 2019

(54) NUTRITIONAL COMPOSITION FOR IMPROVING THE MAMMALIAN IMMUNE SYSTEM

(71) Applicant: N.V. Nutricia, Zoetermeer (NL)

(72) Inventors: Joyce Faber, Goor (NL); Adrianus Lambertus Bertholdus Van Helvoort, Wageningen (NL); Klaske Van Norren, Renkum (NL); Arjan Paul Vos, Bennekom (NL); Robert Johan Joseph Hageman, Wageningen (NL); Cornelus Johannes Petrus Van Limpt, Amersfoort (NL)

(73) Assignee: N. V. Nutricia, Zoetermeer (NL)

(*) Notice: Subject to any disclaimer, the term of this patent is extended or adjusted under 35 U.S.C. 154(b) by 228 days.

(21) Appl. No.: 14/486,184

(22) Filed: Sep. 15, 2014

(65) Prior Publication Data

US 2015/0004130 A1   Jan. 1, 2015

Related U.S. Application Data

(63) Continuation of application No. 12/977,123, filed on Dec. 23, 2010, now abandoned, which is a continuation of application No. PCT/NL2009/050370, filed on Jun. 23, 2009, which is a continuation-in-part of application No. PCT/NL2008/050414, filed on Jun. 23, 2008.

(51) Int. Cl.

| | |
|---|---|
| *A61K 39/39* | (2006.01) |
| *A61K 31/202* | (2006.01) |
| *A61K 31/702* | (2006.01) |
| *A61K 35/20* | (2006.01) |
| *A61K 38/01* | (2006.01) |
| *A61K 38/02* | (2006.01) |
| *A61K 45/06* | (2006.01) |
| *A23L 33/00* | (2016.01) |
| *A23L 33/12* | (2016.01) |
| *A23L 33/175* | (2016.01) |
| *A23L 33/19* | (2016.01) |
| *A61K 31/198* | (2006.01) |
| *A61K 47/12* | (2006.01) |
| *A61K 47/42* | (2017.01) |
| *A61K 39/00* | (2006.01) |

(52) U.S. Cl.
CPC ............ *A61K 39/39* (2013.01); *A23L 33/12* (2016.08); *A23L 33/175* (2016.08); *A23L 33/19* (2016.08); *A23L 33/40* (2016.08); *A61K 31/198* (2013.01); *A61K 31/202* (2013.01); *A61K 31/702* (2013.01); *A61K 35/20* (2013.01); *A61K 38/018* (2013.01); *A61K 38/02* (2013.01); *A61K 45/06* (2013.01); *A61K 47/12* (2013.01); *A61K 47/42* (2013.01); *A23V 2002/00* (2013.01); *A61K 2039/55583* (2013.01)

(58) Field of Classification Search
CPC .... A61K 39/39; A61K 31/202; A61K 31/702; A61K 35/20; A61K 38/018; A61K 38/02; A61K 45/06; A23L 33/40; A23L 33/12; A23L 33/175; A23L 33/19; A23L 2002/00
See application file for complete search history.

(56) References Cited

U.S. PATENT DOCUMENTS

| | | | |
|---|---|---|---|
| 2004/0067224 | A1 | 4/2004 | Ernest |
| 2007/0116802 | A1 | 5/2007 | Germano |

FOREIGN PATENT DOCUMENTS

| | | |
|---|---|---|
| EP | 1629850 A1 | 3/2006 |
| WO | 0215720 A2 | 2/2002 |
| WO | 2004026294 A1 | 4/2004 |
| WO | 2004049830 A1 | 6/2004 |
| WO | 2004062379 A2 | 7/2004 |
| WO | 2007043870 A1 | 4/2007 |
| WO | 2007069900 A1 | 6/2007 |
| WO | 2007145520 | 6/2007 |
| WO | 2007114683 A1 | 10/2007 |
| WO | 2008046870 A1 | 4/2008 |
| WO | 2009157759 A1 | 12/2009 |
| WO | 2009157767 A1 | 12/2009 |

OTHER PUBLICATIONS

Third Party Obervation for corresponding European Patent Application No. 2296643, dated Sep. 26, 2014.
Bell; "Whey protein concentrates with and without immunoglobulins: a review"; Journal of Medicinal Food, vol. 3, No. 1, 2000.
Statement of Jul. 2006 as to the change of composition of Benefiber.
Office Action issued for corresponding European Patent Application No. 2296643, dated Jan. 25, 2017.
Anthony et al.; "Signaling Pathways Involved in Translational Control of Protein Synthesis in Skeletal Muscle by Leucine"; The Journal of Nutrition 2001, vol. 131, pp. 856S-860S.

(Continued)

*Primary Examiner* — Ruixiang Li
(74) *Attorney, Agent, or Firm* — Banner & Witcoff, Ltd.

(57) ABSTRACT

The invention relates to a nutritional composition comprising
(a) at least 18 en % of proteinaceous matter;
(b) at least 12 wt % of leucine, based on total proteinaceous matter;
(c) a lipid fraction comprising at least a ω-3 polyunsaturated fatty acid selected from the group of eicosapentaenoic acid, docosahexaenoic acid, eicosatetraenoic acid and docosapentaenoic acid;
(d) an immune modulator;
for improving the immune function in a mammal, preferably a human.

24 Claims, 2 Drawing Sheets

(56) References Cited

OTHER PUBLICATIONS

Cancer and Nutrition—Why Nutrition is Important—Resource Medical Nutrition from Walgreens Home Delivery—Booklet by Novartis Nutrition from 2003, first and last page.
Da Silva—Nutritional Patient Monitoring—Malignant Neoplasm Breast with Lover Metastasis (in Portugese), Sao Judas Tadeu University, School of Biological and Health Sciences—Published 2007.
Die richtige Grosse gegen tumorbedingte Mangelernahrung: FortiCare mit EPO—Product brochure by Pfrimmer Nutricia.
Faber et al.; "Beneficial immune modulatory effects of a specific nutrtional combination in a murine model for cancer cachexia"; British Journal of Cancer (2008) 99, 2029-2036.
FortiCare Data Sheet.
Forticare Product Brochure.
Gegen tumorbedingte Mangelernahrung—Klinikartz 2004—33(12)—XXV—Georg Thieme Verlag KG—published Jan. 13, 2005.
http://web.archive.org/web/20041l09192247/http://www.forticare.de/cgi-bin/main. pl?page=forticare typanalyse—Nov. 9, 2004.
J.M. Argiles; "Cancer-associated malnutrition"; European Journal pof Oncology Nursing 2005, vol. 9, pp. S39-S50.
Kobayashi et al.; "Modulations of Muscle Protein Metabolism by Branched-Chain Amino Acids in Normal and Muscle-Atrophying Rats"; The Journal of Nutrition 2006, vol. 136, pp. 234S-236S.
Machine translation da Silva.
Marian A.E. van Bokhorst-de van der Schueren; "Nutritional support strategies for malnourished cancer patients"; European Journal of Oncology Nursing 2005, vol. 9, pp. S74-S83.
Neu von Pfrimmer Nutricia: Forti-Care gegen tumorbedingte Mangelemahrung—http://www.nutricia.de/aktuelles/news_archive/neu_von_pfrimmer_nutricia_forticare_gegen_tumorbedingte_mangelemarhrung/.
Norren et al.; "Dietary supplementation with a specific combination of high protein, leucine, and fish oil improves muscle function and daily activity in tumour-bearing cachectic mice"; British Journal of Cancer (2009) 100, 713-722.
Novartis im ersten Halbjahr mit starker Performance und anhaltenden Marktandteilsgewinnen—Media release by Novartis, pp. 1-28, Basel, Jul. 21, 2003.
Numico Annual Report 2004, selected pages.
Philip C. Calder; "N-3 Polyunsaturated fatty acids, inflammation, and inflammatory diseases"; The American Journal of Clinical Nutrition 2006, 83 (suppl) pp. 1505S-1519S.
Photographs of a Forti-Care product sample with an expiry date of Apr. 28, 2007.
Pizato et al; "Fish oil alters T-lymphocyte proliferation and macrophage responses in Walker 256 tumor-bearing rats"; Nutrition 2006, vol. 22, pp. 425-432.
Resource Support—A New advance in Specialized Nutrition for People with Cancer—Summary of Studies in Cancer—Booklet bet Novartis Nutrition from 2003—8 pages.
Resource Support—A state of the art solution for the nutritional management of cancer patients—Product brochure by Novartis Medical Nutrition from 2003, pp. 1-36.
Toomey et al.; "Mechanisms Mediating Cancer Cachexia"; Cancer 1995, vol. 76, No. 12, pp. 2418-2426.
Vos et al.; "Immune-Modulatory Effect and Potential working Mechanisms of Orally Applied Nondigestible Carbohydrates"; Critical Review in Immunology 2007, vol. 27, No. 2, pp. 97-140.
Letter from the Opponent for corresponding European Patent Application No. 2296643, dated Apr. 25, 2018.
FortiCare, product description, Document E38a, http://www.nutricia.nl/medisch/asp/show_group.asp?id:15941&status_id:13&print=. . . Jun. 30, 2004.
Declaration by Dr. Christina Schneid relating to document 38a, Fresenius Kabi Deutschland GmbH dated Apr. 20, 2018.
Excerpt (pp. 1, 5 and 14) from a scientific rationale by Dr. Christina Schneid, Document 39a, Fresenius Kabi Deutschland GmbH dated May 11, 2005.
Declaration by Dr. Christina Schneid relating to document 39a, Fresenius Kabi Deutschland GmbH dated Apr. 20, 2018.
Declaration by Dr. Christina Schneid relating to FortiCare Data Sheet, Fresenius Kabi Deutschland GmbH dated Apr. 20, 2018.
File structure of launch binder by Michaela Ries, Document E41b, Fresenius Kabi Deutschland GmbH, dated Jul. 24, 2007.
Declaration by Michaela Ries relating to document E41b, Fresenius Kabi Deutschland GmbH, dated Apr. 20, 2018.
Screenshot showing the pdf file of document "13e Resource support (Novartis)_product monograph", as well as general properties of this pdf file, screenshot dated Apr. 24, 2018.
Screenshot showing the pdf file of document "13d FortiCare (Nutricia)_data card", as well as general properties of this pdf tile, screenshot dated Apr. 24, 2018.
Salmen et al.; "Amino acids content and electrophoretic profile of camel milk casein from different camels breeds in Saudi Arabia"; Saudi Journal of Biological Sciences (2012) 19, 177-183.
Sindayikengera et al.; "Nutritional evaluation of caseins and whey proteins and their hydrolysates from Protamex"; Univ Science B 2006 7(2):90-98.
Vos et al.; "Dietary supplementation with specific oligosaccharide mixtures decreases parameters of allergic asthma in mice"; International Immunopharmacology 7 (2007) 1582-1587.
Vos et al.; "P0084 PP a Mixture of Galacto and Fructo Oligosaccharides Shows Prebiotic Effects and Enhances Systemic Cellular Immune Responsiveness in Mice"; Journal of Pediatric Gastroenterology and Nutrition, vol. 39, Supplement 1, Jun. 2004, pp. S88-S89.

NUTRITIONAL COMPOSITION FOR IMPROVING THE MAMMALIAN IMMUNE SYSTEM

RELATED APPLICATIONS

This application is a continuation of Ser. No. 12/977,123, filed Dec. 23, 2010; which is a continuation of PCT application number PCT/NL2009/050370 designating the United States and filed Jun. 23, 2009; which claims the benefit of PCT application number PCT/NL2008/050414 and filed Jun. 23, 2008 both of which are hereby incorporated by reference in their entireties.

DESCRIPTION

The invention relates to a composition comprising proteinaceous matter that comprises leucine, an ω-3 polyunsaturated fatty acid and an immune modulator.

The invention also relates to the use of a composition suitable for improving the immune function of a mammal.

The main function of the immune system in mammals is to protect the organism against pathogenic infections and to eradicate (pre-)malignant cells. Immune function is multi-layered and many different cell types are involved. Physical and chemical barriers constitute the first layer of defence against pathogens, an aspect of particular importance at mucosal epithelia such as the gastro-intestinal lining. In addition to immune cells, non-immune cells such as epithelial cells play important roles in this first layer of defence. The innate immune system, consisting mainly of natural killer (NK) cells, phagocytic leukocytes such as granulocytes and macrophages, and antigen presenting cells such as dendritic cells, provides a rapid-acting non-adaptive second layer of defence against pathogens. In interplay with innate cells, T and B cells constitute the adaptive immune system, which is the third layer of defence. It provides adaptive, highly-specific cellular or humoral immune responses and this leads to the formation of immunological memory.

A reduced immune function has consequences for a person's ability to defend against infectious agents. Reduced immune function is characterized by a reduction in the number of immune cells, or an alteration in the function of immune cells that leads to a decrease in their efficiency to protect against pathogens. Severe disease states associated with cancer, tumour growth, diabetes, chronic obstructive pulmonary disease (COPD), HIV-infections (i.e. seropositives), AIDS, renal disease, renal failure, heart failure, and a disease state characterized by a high plasma and/or serum level of pro-inflammatory cytokines may give rise to a reduced immune function of a patient.

In particular in people suffering from such disease or a drug addiction, a reduced immune function may give rise to a worse prognosis with respect to the chance of survival or life expectancy. In many cases it has been shown that, rather than the disease or drug addiction itself, an additional infection is the cause of death. Also, a reduced immune function may be detrimental to the quality of life. Next to that, the presence of an infectious complication might lead to a change in the scheduled treatment of a patient (e.g. a surgery or a therapy with drugs (e.g. chemotherapy) may be postponed).

It is an object of the invention to provide a composition suitable for improving the immune function. In particular it is an object to provide a nutritional composition for such purpose. Improved immune function is in particular defined herein as an enhanced ability to respond to an acute pathogenic stimulus, resulting in an enhanced protective immune response to an exogenous pathogen or to an autologous trigger such as neoplastic cells. Accordingly,

BRIEF DESCRIPTION OF THE DRAWINGS

The foregoing and other features and advantages of the present invention will be more fully understood from the following detailed description of illustrative embodiments taken in conjunction with the accompanying drawings in which.

Figure 1:
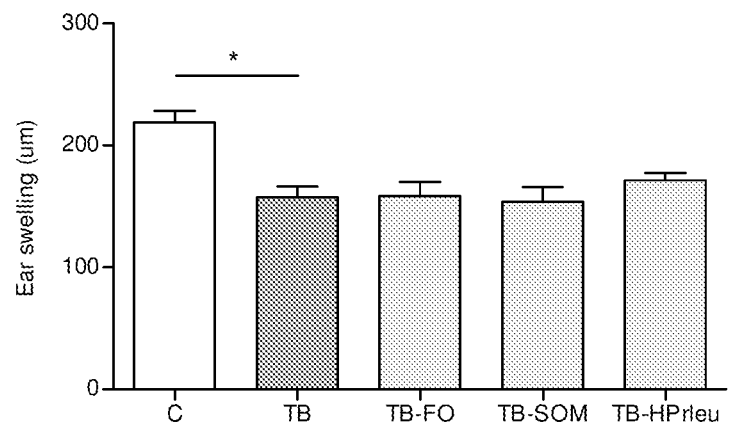
FIG. 1 is graph of the effects of oral administration of fish oil, specific oligosaccharide mixture or high protein/leucine in tumour-bearing mice.

The improved immune function, in particular the improved acute immune function can be an improved cell-mediated immune function, an improved humoral immunity or a combination thereof.

Improved cell-mediated immune function can be measured in a number of ways:
- as enhanced in vivo delayed-type hypersensitivity (including contact hypersensitivity) responses against recall antigens or antigens to which the organism was previously sensitized or vaccinated.
- as enhanced cellular proliferation, cytokine production, oxidative burst response or phagocytic activity in response to pathogen-related, pathogen-mimicking, mitogenic stimuli or antigens which the organism was previously sensitized or vaccinated.

Improved humoral immunity can be determined, e.g. by measuring antibody-levels and/or levels of one or more other markers (e.g. complement protein production) in blood serum. An increase in antibody production in response to pathogenic stimuli or vaccination is a sign of improved humoral immunity.

It has now been found that immune function, in particular acute immune function can be improved by treating a subject, especially a subject with a reduced immune function or being at risk of developing a reduced immune function, with a specific composition comprising proteinaceous matter.

Accordingly, the present invention relates to a nutritional composition, comprising
a) at least 18 en % of proteinaceous matter;
b) at least 12 wt % of leucine, based on total proteinaceous matter;
c) a lipid fraction comprising at least one ω-3 polyunsaturated fatty acid selected from the group of eicosapentaenoic acid, docosahexaenoic acid, eicosatetraenoic acid and docosapentaenoic acid;
d) an immune modulator.

The energetic value of a compound (en %) is based on the energy provided by the digestible part (in particular in a human) of the compound. In particular the energetic value is based on the contribution of proteinaceous matter, lipids and digestible carbohydrates, using the following calculation factors: 4 kcal/g for digestible carbohydrates and proteinaceous matter and 9 kcal/g for lipids.

The composition is in particular suitable for improving the immune function in a mammal. When referring to a composition comprising said components a), b), c) and d) for a specific purpose it is in particular meant that said components a), b), c) and d) are intended to be used for that purpose in combination. Accordingly, each of said components is considered to play a role in accomplishing that purpose. Thus, the invention is in particular directed to a composition wherein a combination of said components a), b), c) and d) is for improving the immune function in a mammal.

In particular a composition of the invention may be used to improved immune function in that the ability to respond to an acute pathogenic stimulus is enhanced. More in particular, the invention provides a composition for enhancing protective immune response to an exogenous pathogen or to an autologous trigger such as neoplastic cells. Accordingly, a composition according to the invention in particular may be used as a prophylactic, e.g. to avoid an infection or reduce the severity of an infection or another immune-related disease.

In a specific embodiment, the composition according to the invention is used for the treatment of neutropenia, in particular chemotherapy-induced neutropenia.

Compositions comprising proteinaceous matter and an immunomodulator are known in the art per se. For instance, WO 2007/145520 relates to an anti-inflammatory composition comprising glycine (an immunomodulator) and a transferrin protein. The composition optionally comprises an anti-inflammatory polyunsaturated fatty acid. The use of such compositions to treat inflammations is mentioned, but it is not specifically mentioned to improve immune function.

The composition optionally comprises leucine. Its stated purpose is for management of muscle wasting.

Preferably, the organoleptic properties of the composition is such that the consumption is generally appreciated as pleasant.

Preferably, the composition passes the stomach easily.

Preferably, the digestible components of the composition becomes readily available upon intake of the product.

A composition according to the invention may in particular be used to improve a T-helper1 (Th1) mediated immune response in a mammal.

It is understood that improving a Th1-mediated immune response may comprise improving cellular vaccination responses; increasing Th1-induced production of IgG subclass antibody production in acute responses against pathogens or in anti-tumour immune responses (e.g. IgG1 in humans, IgG2a in mice); decreasing antigen-specific or total IgE antibodies in serum; improving cellular immune responses to viral or bacterial pathogens or pathogen-mimicking substances; increasing IL-2, IFN-gamma or IL-12 production in acute responses against pathogens, pathogen-mimicking substances or in local anti-tumour immune responses.

A composition according to the invention may also be used to reach an effect that may be selected from the group of increasing the activity or number of natural killer (NK) cells; increasing pathogen-specific or tumour-specific IgA, IgG or IgM antibody production; increasing IgA, IgG or IgM concentrations to normal range values in the blood of mammals with sub-normal levels of said antibodies; increasing the total number of white blood cells in mammals with treatment- or disease-induced decreased number of white blood cells; increasing the number or activity of phagocytic cells in mammals with treatment- or disease-induced decreased number of phagocytic cells; improving cell-mediated cytotoxic responses against pathogens, pathogen-infected cells or tumour cells; improving the barrier function of mucosal epithelia by increasing sIgA excretion; increasing intestinal mucus production; decreasing epithelial permeability or decreasing microbial translocation across the epithelia with the exception of non-infectious uptake of microbes by local immune cells; improving the composition of the intestinal microbiota by increasing the number or activity of beneficial bacteria such as bifidobacteria or lactobacilli, by improving the colonization resistance of the intestinal microbiota, by decreasing the number of potential pathogenic organisms in the intestinal microbiota, or by decreasing the pH of the intestinal content.

In an embodiment, a composition of the invention may be used to prevent or treat a reduced immune function due to, or resulting from aging, disease, disorder or trauma, preferably disease, disorder or trauma.

Reduced immune function may in particular manifest itself as a symptom selected from the group of infections, inflammations, vascular complications, bad wound healing, mucositis and stomatitis.

Involuntary weight loss and sarcopenia may further deteriorate the immune function of a mammal.

A composition of the invention may in particular be used for treating a mammal suffering from a disease or disorder selected from the group of cancer, tumour growth, diabetes, chronic obstructive pulmonary disease, HIV-infections, renal disease, renal failure, heart failure, and a disease state characterized by a high plasma and/or serum level of pro-inflammatory cytokines. Most preferably, the disease is cancer.

In an embodiment wherein a composition according to the invention is used to treat trauma, the trauma may in particular be selected from the group of surgery, drug treatment, chemotherapy and radiotherapy.

Based on experiments wherein compositions according to the invention are fed to tumour-bearing mice, as illustrated in the example below, it is contemplated by the inventors that a composition of the invention is effective in improving the immune system of a mammal. It was shown in the experiments that at least one of several physiological and immune parameters associated with a reduced immune function was positively affected, indicating a better immune response of the mammal. In particular, hypersensitivity response (in vivo cellular immune response) may be improved. Further, based on the experimental results it is contemplated that one or more immune functions related to the thymus functioning may be improved (e.g. T-lymphocyte maturation, thymus output of mature naive T-lymphocytes or improved protection against autoimmunity). Increase of thymus weight in test animals treated with a composition according to the invention compared to a control group is considered an indicator for such improved immune function.

It is further contemplated that a composition of the invention may be used to provide a better prognosis in terms of extended life-expectancy and/or a better quality of life. Factors improving the quality of life are in particular less fatigue, more stamina, less complications such as viral and/or bacterial infections (in particular in mouth, throat, intestine, wounds and lungs), reduced loss of visual capability and/or hearing, better general condition and less periods of feeling depressed.

It was further found that a composition of the invention may reduce wasting of fat and lipid stores. Accordingly, the inventors contemplated that a composition of the invention may in particular be used to treat a mammal suffering from an undesired loss of body weight (over 5% in 3 months) or in a mammal running a serious risk to be confronted with such loss.

The composition is in particular suitable for enhancing the effectiveness of an immunotherapy in mammals receiving an anti-cancer immuno-therapy or planning to start anti-cancer immunotherapy within a period of two months.

Immune Modulator

With an immune modulator is meant an agent capable of modifying a function of the immune system.

In a preferred embodiment, the immune modulator is selected from the group of immune system modulating indigestible carbohydrates, lactoferrin, glycine, immune system modulating drugs, and immune system modulating bacteria or fragments thereof.

The immune modulator is typically present in an effective amount, which depends on the particular immune modulator or immune modulators present in the composition.

In particular, one or more immune modulating indigestible carbohydrates are present in a composition of the invention.

In a preferred composition, an immune modulating indigestible carbohydrate is selected from the group of galactooligosaccharides (GOS) and fructooligosaccharides (FOS).

In particular, the galactooligosaccharide is selected from the group of short-chain galactooligosaccharides, long-chain galactooligosaccharides, or any combination thereof.

In particular, the fructooligosaccharide is selected from the group of short-chain fructooligosaccharides, long-chain fructooligosaccharides, or any combination thereof.

A preferred composition comprises a galactooligosaccharide and a fructooligosaccharide.

Preferably, the molar ratio of galactooligosaccharide to fructooligosaccharide is at least 1:1, more preferably at least 5:1. Preferably, the molar ratio of galactooligosaccharide to fructooligosaccharide is 20:1 or less, more preferably from 12:1 or less. In a preferred embodiment, the molar ratio of galactooligosaccharide to fructooligosaccharide ranges from 1:1 to 20:1, preferably from 5:1 to 12:1. In a particularly preferred embodiment, the molar ratio of galactooligosaccharide to fructooligosaccharide is about 9:1.

With an oligosaccharide is meant a chain comprising 2 to 25 saccharide residues.

With a long chain oligosaccharide is meant an oligosaccharide chain comprising 10-25 saccharide residues. With a short chain oligosaccharide is meant an oligosaccharide chain comprising 2-9 saccharide residues, for example 2-5 residues or 6-9 residues.

Indigestible carbohydrates are carbohydrates that remain in essence undigested in the human intestines. In particular, a carbohydrate is considered indigestible in case less than 10% of the sugars is released within 20 and 120 min in an analysis setting using standard digestive enzymes, as determinable by the Enquist method.

In a particular embodiment, the indigestible carbohydrate is selected from the group of galactomannans having a degree of polymerisation (DP) between 2 and 50, xylans with a DP of 2 to 60, oligomers having more than 30 wt % of galacturonic acid or glucuronic acid moieties having a molecular weight of 520-2200 Dalton, and any combination thereof.

In an embodiment, the indigestible carbohydrate content is at least 1 wt %, at least 2 wt % or at least 3 wt %, based on total dry matter. In an embodiment, the indigestible carbohydrate content amounts 15 wt % or less, preferably 12 wt % or less, more preferably 10 wt % or less, based on total dry matter. In a specific embodiment, the indigestible carbohydrate content ranges from 1 to 15 wt %, preferably from 2 to 12 wt %, more preferably from 3 to 10 wt %, based on total dry matter.

In an embodiment, the composition of the invention comprises one or more immune modulators selected from the group of growth factors for preventing or treating neutropenia (granulocytopenia) and growth factor for treatment-related dysfunction of the immune system in cancer patients. In particular such factors are selected from the group of 1) granulocyte-colony stimulating factor (G-CSF) and derivatives thereof, such as Filgrastim, Neupogen, Pegfilgrastim and Neulasta, 2) granulocyte macrophage-colony stimulating factor (GM-CSF), such as Sargramostim, Leukine, Molgramostim, and 3) stem cell factor (SCF), such as Ancestim and StemGem.

In an embodiment, the composition of the invention comprises one or more immune modulators selected from the group antibiotics suitable for the prevention or treatment of infections in cancer patients with neutropenia or anti-cancer treatments that render them susceptible to infections.

In an embodiment, the composition of the invention comprises one or more immune modulators selected from the group immune system modulating bacteria or derivatives thereof, selected from the group of probiotic bacteria, bacterial fragments, CpG oligonucleotides and heat-shock proteins.

An example of a therapy that makes use of an immune modulator is anti-cancer immunotherapy intervention. Such intervention is aimed at stimulating the mammal's immune system to mount effective immune responses against cancer cells, either as a primary treatment or as an adjuvant treatment to eradicate residual cancer cells.

In a specific embodiment of the present invention, the composition according to the invention comprises a mixture of neutral and acid oligosaccharides as disclosed in WO 2005/039597 (N.V. Nutricia), which is incorporated herein by reference in its entirety. More in particular, the acid oligosaccharide has a degree of polymerization (DP) between 1 and 5000, preferably between 1 and 1000, more preferably between 2 and 250, even more preferably between 2 and 50, most preferably between 2 and 10. If a mixture of acid oligosaccharides with different degrees of polymerization is used, the average DP of the acid oligosaccharide mixture is preferably between 2 and 1000, more preferably between 3 and 250, even more preferably between 3 and 50. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). The acid oligosaccharides are preferably characterized by a degree of methoxylation above 20%, preferably above 50% even more preferably above 70%. Preferably the acid oligosaccharides have a degree of methylation above 20%, preferably above 50% even more preferably above 70%. The acid oligosaccharide is preferably administered in an amount of between 10 mg and 100 gram per day, preferably between 100 mg and 50 grams per day, even more between 0.5 and 20 gram per day.

The term neutral oligosaccharides as used in the present invention refers to saccharides which have a degree of polymerization of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used in the present invention preferably refers to saccharides which have a degree of polymerization of the oligosaccharide below 60 monose units, preferably below 40, even more preferably below 20, most preferably below 10. The term monose units refers to units having a closed ring structure, preferably hexose, e.g. the pyranose or furanose forms. The neutral oligosaccharide preferably comprises at least 90%, more preferably at least 95% monose units selected from the group consisting of mannose, arabinose, fructose, fucose, rhamnose, galactose, -D-galactopyranose, ribose, glucose, xylose and derivatives thereof, calculated on the total number of monose units contained therein. Suitable neutral oligosaccharides are preferably fermented by the gut flora. Preferably the oligosaccharide is selected from the group consisting of: cellobiose (4-O-β-D-glucopyranosyl-D-glucose), cellodextrins ((4-O-β-D-glucopyranosyl)$_n$-D-glucose), B-cyclo-dextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructo furanoside), D-agatose, D-lyxo-hexylose, lactosucrose (O-β-D-galactopyranosyl-(1-4)-O-α-D-glucopyranosyl-(1-2)-β-D-fructofuranoside), α-galatooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)-[β-D-glucopyranosyl]$_n$-(1-4) α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactose I, II and III), fructans-Levan-type (β-D-(2→6)-fructofuranosyl)$_n$ α-D-glucopyranoside), fructans-Inulin-type (β-D-((2→1)-fructofuranosyl)$_n$ α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides and mixtures thereof. Most preferably, the neutral oligosaccharide is selected from the group consisting of fructooligosacchararides, galactooligosaccharides and transgalactooligosaccharides.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the composition according to the invention comprises an acid oligosaccharide with a DP between 2 and 250, prepared from pectin, alginate, and mixtures thereof; and a neutral oligosaccharide, selected from the group of fructans, fructooligosaccharides, indigestible dextrins, galactooligosaccharides including transgalacto-oligosaccharides, xylooligosaccharides, arabinooligosaccharides, glucooligosaccharides, mannooligosaccharides, fucooligosaccharides, and mixtures thereof.

In a further preferred embodiment the composition according to the invention comprises two chemically distinct neutral oligosaccharides. It was found that the administration of acid oligosaccharides combined with two chemically distinct neutral oligosaccharides provides an optimal synergistic immune stimulatory effect.

Preferably the composition according to the invention comprises:
- an acid oligosaccharides as defined above;
- a galactose-based neutral oligosaccharide (of which more than 50% of the monose units are galactose units), preferably selected from the group consisting of galactooligosaccharide and transgalactooligosaccharide; and
- a fructose and/or glucose based neutral oligosaccharide (of which more than 50% of the monose units are fructose and/or glucose, preferably fructose units), preferably inulin, fructan and/or fructooligosaccharide, most preferably long chain fructooligosaccharide (with an average DP of 10 to 60).

The mixture of acid- and neutral oligosaccharides is preferably administered in an amount of between 10 mg and 100 gram per day, preferably between 100 mg and 25 grams per day, even more preferably between 0.5 and 20 gram per day.

Proteinaceous Matter

Proteinaceous matter is formed by moieties formed from amino acids. The term amino acids as used herein includes amino-acid residues (e.g. in peptides). In particular the term 'proteinaceous matter' includes free amino acids, amino acid salts, amino acid esters, the amino acid residues bound to conjugating molecules and peptides, including proteins. Likewise, when reference is made to a specific amino acid, e.g. leucine, this is meant to include the specific amino acid (residues) present as a salt, in a bound form, as well as the free specific amino acid.

With a peptide is meant a combination of two or more amino acids, connected via one or more peptidic bonds. When incorporated in a peptide, amino acids are named amino-acid residues. Peptides include oligopeptides and polypeptides, including proteins.

With a polypeptide is meant a peptide chain comprising 14 or more amino-acid residues. With an oligopeptide is meant a peptide chain comprising 2 to 13 amino-acid residues.

Chiral amino acids present in a composition of the invention may be in the L-form or the D-form. Usually, the chiral amino acids present in a composition of the invention are in the L-form.

In an embodiment, a liquid composition according to the invention comprises at least 7 g/100 ml of proteinaceous matter, preferably at least 8 g/100 ml, more preferably at least 9 g/100 ml, most preferably at least 10 g/100 ml.

The proteinaceous matter in a composition of the invention provides at least 18 en %, preferably at least 20 en %, more preferably at least 22 en % of the total composition. The proteinaceous matter in a composition of the invention usually provides 50 en % or less, preferably 40 en % or less, or more preferably 32 en % or less of the total composition.

The proteinaceous matter preferably comprises at least one protein source selected from the group of whey, casein, caseinate, soy and wheat, preferably from the group of whey and casein. Said protein source or part thereof may have been modified, in particular by (partial) hydrolysis.

With whey is meant a source of a globular proteins that can be isolated from whey. In particular, globular whey proteins can be selected from beta-lactoglobulin, alpha-lactalbumin and serum albumin, including mixtures thereof. Examples of mixtures that comprise whey proteins are whey isolate and whey concentrate.

In an embodiment, the proteinaceous matter comprises whey, in particular at least 10 wt. % based upon the proteinaceous matter, preferably at least 15 wt. % based upon the proteinaceous matter. Usually, the whey fraction is 50 wt. % or less based on proteinaceous matter, in particular 40 wt. % or less based on proteinaceous matter.

In particular in case of a liquid composition, the concentration of denaturated whey preferably does not exceed 35 wt. % based upon the proteinaceous matter. This is advantageous with respect to avoiding the risk of gelation during storage.

The presence of a whey may offer a number of advantages. The whey shows an advantageous release behaviour both in terms of release rate of the amino acids and the tendency to make the amino acids available for uptake by the body, essentially at the same time.

The advantageous amino-acid release behaviour may be further enhanced by (slightly) hydrolysing at least part of the whey, usually to the extent that up to 20% of the protein is hydrolysed to free amino acids, preferably to the extent that up to 10% of the protein is hydrolysed to free amino acids.

For said enhanced effect usually 50 wt % of the whey or less is (slightly) hydrolysed, in particular 10-50 wt %.

If desired the free amino acid or part thereof may be removed from the hydrolysate. Suitable techniques are known, e.g. filtration, chromatography or absorption.

As the source for whey proteins preferably a whey fraction is chosen comprising less that 20 wt % casein glycomacropeptide (GMP), more preferably less than 10 wt %.

The beta-lactoglobulin content preferably is larger than 40 wt %, more preferably 46-80 wt %. This is advantageous as beta-lactoglobulin has a relatively high leucine content.

When used as intact protein, the casein preferably comprises a high concentration of beta casein, in particular more than 36 g/100 g casein, more in particular 38-70 g/100 g casein.

In an embodiment, at least part of the proteinaceous matter is present in the form of free amino acids, a salt thereof or as a conjugate with a conjugating molecule other than a protein or peptide, which conjugate is capable of being split in the free amino acid (or salt thereof) and the conjugating compound under the influence of a bile constituent and/or a pancreas excretia in duodenum and/or the ileum. In an embodiment, the amount of amino acid in such form, in particular in the form of a salt or the free form, is up to 15 wt % based on the proteinaceous matter, preferably 0.5-14 wt %.

The peptide content (oligopeptide, polypeptide, protein) based on proteinaceous matter is usually at least 50 wt %, at least 60 wt % or at least 75 wt %. The wt % of peptide based on proteinaceous matter is usually up to 99 wt %, preferably up to 94 wt %, more preferably 89 wt %.

An advantage of a composition wherein the peptide content is high (≥50 wt %) is that the taste, or another organoleptic property of the composition, usually is appreciated better when consumed (orally). Further, the uptake of amino acids by the body may be more gradual.

In a particular embodiment, the composition comprises leucine in the form of a free acid, a salt, a dipeptide or a conjugate with a conjugating compound other than an amino acid, a protein, or a peptide, which conjugate is capable of being split into the free amino acid (or salt thereof), preferably in the gut or stomach or after absorption in the enterocytes or liver.

Leucine is preferably for at least 35 wt %, more preferably for at least 40 wt %, based on the total proteinaceous leucine, present in the form of a peptide (oligopeptide, polypeptide, protein), preferably in the form of polypeptides and/or (intact) proteins.

Leucine is for up to 100 wt %, preferably for up to 80 wt %, based on the total proteinaceous leucine, present in the form of a peptide (oligopeptide, polypeptide, protein), more preferably in the form of one or more polypeptides and/or one or more (intact) proteins.

The leucine content in a composition of the invention is at least 12 wt %, at least 13 wt %, at least 16 wt. % or at least 19 wt %, based on total proteinaceous matter. Usually the leucine content is 50 wt % or less, in particular it may be 30 wt % or less, 25 wt % or less or 23 wt % or less, based on total proteinaceous matter. In an embodiment, the leucine content is 12 to 23 wt %, based on total proteinaceous matter.

Advantageously, the composition may comprise glutamine.

If present, the glutamine content is at least 4 wt %, preferably at least 5 wt %, based on total proteinaceous matter. In an embodiment, the glutamine content is 4 to 20 wt %, preferably 5 to 10 wt %, based on total proteinaceous matter.

Advantageously, the composition may comprise one or more of the group of cystine, cysteine and cysteine equivalents such as N-acetyl cysteine. preferably in an amount of at least 0.8 wt %, based on total proteinaceous matter. Usually the content of cystine, cysteine and cysteine equivalents is 11 wt % or less, in particular it is 8 wt % or less, based on total proteinaceous matter. In an embodiment, the content of cystine, cysteine and cysteine equivalents is 0.8 to 8 wt %, based on total proteinaceous matter.

Glutathione homeostasis of leucocytes plays a role in the functioning of the immune system. In experiments with tumour-bearing mice, the inventors found that glutathione levels of the liver were significantly decreased. Surprisingly, further experiments by the inventors revealed that at least partial normalisation of the glutathione level in liver cells occurred under the influence of glutamine and/or cysteine in a composition of the invention. Particularly good results were obtained when both amino acids were present in the composition.

Based on these experiments, it is contemplated by the inventors that a composition of the invention comprising glutamine or cysteine, preferably in a concentration as indicated above, is particularly effective in improving the immune system of a mammal. It is further contemplated that the presence of both glutamine and cysteine in a composition of the invention is even more effective in improving the immune system of a mammal.

In an embodiment, an advantageous effect of glutamine and/or cysteine on the immune system of a mammal is obtained with a composition of the invention comprising whey protein and casein.

In a composition according to the invention the weight ratio leucine/(valine+isoleucine) is generally 1.0 or more, preferably 1.05 or more.

In the total product the content of essential amino acids usually is at least 49 wt %, preferably 49-80 wt %, more preferably 52-70 wt % of the proteinaceous matter is formed by essential amino acids.

The lysine content usually is 7.0-15 g/100 g proteinaceous matter, preferably 7.5 to 14 g/100 g proteinaceous matter.

Lipid Fraction

In a composition of the invention, the lipid fraction usually provides at least 10 en %, preferably at least 20 en % or more preferably at least 25 en % of the total composition. The lipid fraction in a composition of the invention usually provides 50 en % or less, preferably 40 en % or less, or more preferably 35 en % or less of the total composition.

With the term 'lipid fraction' is meant a fraction comprising one or more lipids, including fatty acids, fatty-acid derivatives (including tri-, di-, and monoglycerides and phospholipids) and sterol-containing metabolites such as cholesterol.

As indicated above, a composition of the invention comprises at least one ω-3 polyunsaturated fatty acid selected from the group of eicosapentaenoic acid (EPA), docosahexaenoic acid (DHA), eicosatetraenoic acid (ETA) and docosapentaenoic acid (DPA).

A composition of the invention may further comprise ω-3 and/or ω-6 polyunsaturated fatty acids, in particular those containing 18 to 26 carbon atoms, e.g. linolenic acid (LA), alpha linolenic acid (ALA), gamma linolenic acid (GLA), dihomo gamma-linolenic acid (DGLA) and arachidonic acid (AA).

For obtaining an advantageous effect on immune function, the ω-3 unsaturated fatty acid content is usually at least 10 wt %, preferably at least 15 wt %, based on total lipid content.

In a further embodiment, the composition of the invention comprises stearidonic acid (SDA). Nutritional oils containing SDA are reported to be a dietary source of ω-3 fatty acids that would be more effective in increasing tissue EPA and DPA concentrations than are current ALA-containing oils. Preferably, the lipid fraction in the composition comprises more than 0.5 wt % of SDA, more preferable more than 0.6 wt % of SDA, still more preferably more than 1.2 wt % of SDA, based on total lipid. The maximum amount is more or less limited by the particular source used (type of marine oil), but marine oils with an SDA amount of 2 wt % to about 5 wt % (based on total lipid in the latter oil) are commercially available. Preferably, the amount of SDA in the lipid fraction ranges between 0.5 and 5 wt %, based on total lipid. It is preferred that the amount of SDA is relatively high compared to that of docosahexaenoic acid (DHA) and/or linoleic acid (LA). This allows a high efficacy and manufacture of palatable products comprising low amounts of oxidized products. In effective embodiments of the product according the invention the weight ratio of SDA to DHA is therefore at least 0.22, preferably at least 0.25, more preferably at least 0.30.

A composition of the invention may in particular be a composition wherein at least 55 wt % of the lipid fraction, preferably triglyceride oils, comprise at least 4 wt % of one or more of eicosapentaenoic acid and docosahexaenoic acid.

In a composition of the invention, the lipid fraction comprises less than 30 wt % of a saturated fatty acid, preferably less than 22 wt %, based on total lipid content.

The ratio ω-3 to ω-6 polyunsaturated fatty acids can be chosen within wide limits, e.g. from 0.2 to 10, or from 0.4 to 3.0. In particular, the ratio ω-3 to ω-6 polyunsaturated fatty acids is less than 1.0, preferably 0.97 or less, more preferably 0.95 or less. The ratio is preferably larger 0.5 or more, more preferably 0.6 or more. In particular, preferably the ratio is from 0.5 to 0.97, more preferably from 0.6 to 0.95.

Carbohydrate Fraction

In an embodiment, a composition of the invention comprises a digestible carbohydrate fraction, providing at least 20 en %, preferably at least 30 en % or more preferably at least 38 en % of the total composition.

The digestible carbohydrate fraction in a composition of the invention usually provides 70 en % or less, preferably 60 en % or less, more preferably 48 en % of the total composition.

With the term 'digestible carbohydrate' fraction is meant a fraction comprising one or more digestible carbohydrates.

Digestible carbohydrates include maltodextrose, maltose and glucose. In particular, a carbohydrate is considered digestible in case more than 90% of quickly carbohydrates are digested within 20 min in accordance with the Enquist method.

Especially the composition of the carbohydrate fraction may be chosen to achieve a favourable carbohydrate uptake, and accordingly a desirable insulin release after intake. Accordingly, in particular a composition meeting one or more of the following criteria with respect to the carbohydrate content are considered to be advantageous.

In an embodiment less than 75 wt. % of the carbohydrates is formed by the sum of the sucrose and the maltodextrin content.

In an embodiment at least 40 wt % based on the total weight of the carbohydrates is formed by slowly digestible carbohydrates, i.e. in particular carbohydrates which are digested less fast than maltodextrose, maltose and glucose In an embodiment a composition according to the invention comprises less than 60 wt. %, preferably 20-50 wt. % based on the total weight of the carbohydrates of quickly digestible carbohydrates, in particular of maltodextrose, maltose, glucose and other carbohydrates which are digested at least as fast.

In an embodiment more than 20 wt. % based on the total weight of the carbohydrates is formed by at least one disaccharide, preferably 22-60 wt. %. In particular in such an embodiment, the disaccharide is preferably selected from the group consisting of sucrose, trehalose, palatinose, lactose and other low glycaemic disaccharides, more preferably from trehalose and palatinose.

In an embodiment at least one monosaccharide other than glucose is present. Preferably said monosaccharide is selected from the group consisting of galactose, mannose and ribose. Preferably the total amount of said monosaccharide(s) is 0.5-30 wt. %, more preferably 5-25 wt. % based on the total weight of the carbohydrates.

In particular, the presence of ribose is advantageous, preferably in combination with (endogenous) folic acid, to increase the protein synthesis. It is contemplated that the combination of these two compounds allows an increase in the production of guanosine triphosphate in the mammal, resulting in an increase of the protein synthesis via stimulation of eukaryotic initiation factor 2B, especially in malnourished patients. The folic acid may be provided in one or more of the following forms: free folic acid, folinic acid, formylated folic acid, methylated folic acid, preferably in a reduced form or as a mono- or polyglutamate conjugated derivative. When present, the folic acid content is usually at least 95 µg per 100 kcal carbohydrates, preferably 110-400 µg per 100 kcal carbohydrates, more preferably 125-300 µg per 100 kcal carbohydrates.

It is contemplated that it is advantageous with respect to improving immune function, especially cellular immune function, that the composition has a relatively low glycaemic index. A composition having a low glycaemic index is also considered advantageous in that it may have a higher effectivity with respect to avoiding or at least reducing the number, reducing the severity of infections, or avoiding or at least reducing complications related to infections (e.g. inflammation as a result of an infection). Further, it is contemplated that a low glycaemic index of a composition according to the invention may contribute to avoiding inflammation reactions or reduce the severity thereof. In particular, without being bound by theory, it is thought that the occurrence of high glucose peaks in blood after administration of a (conventional) composition having a high glycaemic index may contribute to initiating chronic inflammation or may make an existing chronic inflammation more severe. This may in turn give rise to a suppression of (cellular) immunity. Since the administration of a composition with a low glycaemic to a subject typically gives rise to a more gradual release of glucose in the blood, it is thought that a composition with a relatively low glycaemic index may have improved effectivity, compared to a product having a relatively high glycaemic index, at least in specific embodiments.

Accordingly, in a specific embodiment, the composition is a nutritional composition with a low glycaemic index. In particular it is considered advantageous that the glycaemic index of the composition is below 55, in particular below 50, preferably below 45. In practice, the glycaemic index (of a composition comprising digestible carbohydrate) will be above zero, and usually be at least 1, in particular at least 5. Details on how to determine the glycaemic index of a composition are provided in the Examples, herein below.

The skilled person will be able to formulate a composition with a relatively low glycaemic index based on the information disclosed herein and common general knowledge. In particular, by increasing the percentage of carbohydrate that is digested more slowly than glucose or by increasing carbohydrates that provide less glucose moieties per weight than glucose, the glycaemic index of a composition (under otherwise the same condition) is decreased. Preferred examples of carbohydrates which are digested more slowly than glucose are isomaltulose, fructose, galactose, lactose, trehalose. Next to that addition of fat and fibre can slow down gastric emptying. Moreover, fibres can form a physical barrier in the intestine, reducing absorption rate. Amino acids from protein can increase insulin release (especially leucine), and thereby increase glucose uptake by the cells. All these mechanisms can contribute to a reduction in glycaemic index.

Nutritional Composition

With a nutritional composition is meant a composition that comprises naturally occurring components, preferably found in the food supply, that can be sold over the counter, as supplements, functional foods or food ingredients i.e. without a physician's or veterinarian's prescription. A nutritional composition may also be a medical food, intended for the dietary management of a disease or condition for mammals under the supervision of a physician or veterinarian.

A composition according to the invention may be in the form of a liquid, e.g. a drink, in the form of a semi-liquid, e.g. a yoghurt or a custard, in the form of a gel, e.g. jelly cake or in the form of a solid, e.g. a candy bar or an ice-cream.

In an embodiment, a liquid composition is prepared from a concentrate, e.g. from a liquid (e.g. with a viscosity of less than about 80 mPa·s), a semi-liquid (e.g. with a viscosity of more than about 80 mPa·s and less than about 400 mPa·s), a gel or a solid. For such preparation, water may be used to dilute the concentrate. In particular, such preparation occurs just before administration of the composition, e.g. in an instant-fashion.

One particular embodiment of the invention is a nutritional composition comprising proteinaceous matter, a lipid, and a digestible carbohydrate, wherein
 a) the proteinaceous matter content provides 18 to 50 en %, preferably 20 to 40 en %, more preferably 22 to 32 en % of the total composition;
 b) the lipid content provides 10 to 50 en %, preferably 20 to 40 en %, more preferably 25 to 35 en % of the total composition;
 c) the digestible carbohydrate content provides 20 to 70 en %, preferably 30 to 60 en %, more preferably 38 to 48 en % of the total composition.

The total energetic value of a liquid composition in accordance with the invention may be chosen within wide limits, e.g. from 0.2 to 4 kcal/ml. Usually it is at least 0.3 kcal/ml, in particular at least 0.8 kcal/ml, more in particular at least 1.2 kcal/ml. Usually, it is 3.0 kcal/ml or less, in particular 2.6 kcal/ml or less, more in particular 2.4 kcal/ml or less. In a specific embodiment, the liquid composition in accordance with the invention has an energetic value in the range of 0.3 to 3.0 kcal/ml, preferably 0.8 to 2.6 kcal/ml, more preferably 1.2 to 2.4 kcal/ml.

In another specific embodiment, the liquid composition in accordance with the invention has an energetic value in the range of 0.2 to 1.0 kcal/ml, preferably 0.4 to 0.9 kcal/ml.

Factors that play a role in determining a desirable energetic value include the ease of achieving a higher en % proteinaceous matter on the one hand and a fast emptying of the stomach (increasing anabolic response) on the other hand.

The total energetic value of a semi-liquid, gel or solid composition in accordance with the invention may be chosen within wide limits, e.g. from 1 to 15 kcal/g. Usually, it is at least 2.0 kcal/g, preferably at least 2.8 kcal/g, even more preferably at least 3.2 kcal/g. Usually, it is 12 kcal/g or less, preferably 10 kcal/g or less, even more preferably 8.0 kcal/g or less. In a specific embodiment, the semi-liquid, gel or solid composition in accordance with the invention has an energetic value in the range of 3.2 to 8.0 kcal/g.

Additional Components

In an embodiment, the composition may comprise one or more other additional components such as at least one component selected from the group consisting of minerals, trace elements and vitamins, preferably selected from the group consisting of sodium, potassium, chloride, fluoride, iodide, calcium, phosphorous, magnesium, vitamin A, vitamin D3, vitamin E, vitamin K, vitamin B1, vitamin B2, vitamin B3, vitamin B5, vitamin B6, folic acid, vitamin B12, biotin, vitamin C, lipoic acid, zinc, iron, copper, manganese, molybdenum selenium and chromium.

Such components may be present in a concentration up to the daily recommended dose per daily serving.

Zinc is preferably present in a concentration of at least 2.8 mg per 100 kcal carbohydrates, more preferably of 5.6-20 mg per 100 kcal carbohydrates, even more preferably of 6-15 mg per 100 kcal carbohydrates.

Sustained Release Preparation

In a preferred embodiment, the composition in accordance with the invention further comprises a sustained release preparation effective to release an amino acid in the duodenum and/or the ileum, said preparation comprising at least one component selected from the group consisting of amino acids in the form of a free acid, amino acids in the form of a salt and amino acids in the form of a conjugate with a conjugating compound other than a protein which conjugate is capable of being split in the free amino acid (or salt thereof) and the conjugating compound under the influence of a bile constituent and/or a pancreas excrements in duodenum and/or the ileum.

The amino acid in the sustained release form is preferably suspended in a liquid, semi-liquid or solid product.

The sustained release preparation can be made based upon conventional techniques. The amino acid(s) may be coated with a pH sensitive material that dissolves at the pH existing in the duodenum/ileum (about pH 7) but not in the stomach (strongly acidic). Such coatings are generally known in the art. Examples of conjugating molecules are molecules forming specific peptides with the amino acid that are not split by pepsin, or at least not efficiently split under physiological conditions. Examples are choline, betain, dimethylglycine and sarcosine. Other suitable conjugating molecules include phospholipids, lyso-phospholipids and glycerol.

Amino acids that are preferably present in the sustained release preparation are preferably selected from leucine and other essential amino acids, in particular methionine, arginine, tryptophan, phenylalanine and lysine, of which leucine is especially preferred.

In an advantageous embodiment, a composition according to the invention is administered in a drug regimen. In particular the composition can be used as adjuvant of a drug, such as a drug selected from the group consisting of anti-cancer drugs, anti-retroviral drugs, antihypertensives, anti-thrombotics, anti-depressants and anti-diabetic drugs. In particular, it is advantageous to use the product with metformin or another anti-diabetic drug. These drugs in particular are considered to be stable in a composition according the invention and to be very effective. Said drug may be present in the composition according to the invention or be administered separately.

The invention further relates to a method for improving the immune system of a mammal, comprising administering a nutritional composition comprising at least 18 en % of proteinaceous matter having a leucine content of at least 9.5 wt % based on total proteinaceous matter, a lipid fraction comprising at least one ω-3-polyunsaturated fatty acid selected from the group of eicosapentaenoic acid (EPA), docosahexaenoic acid (DHA), eicosatetraenoic acid (ETA) and docosapentaenoic acid (DPA), and an immune modulator.

The compositions of the invention may be administered under the supervision of a medical specialist, or may be self-administered.

The composition may be administered enterally or orally.

The mammal preferably is a human.

The invention will now be illustrated on the basis of the following examples.

EXAMPLES

Example 1

Materials and Methods

Animals and Diets.

Six to seven-week old syngenic male CD2F1 mice (BALB/c×DBA/2) were obtained from Harlan Nederland (Horst, The Netherlands). All experimental procedures were approved by the Animal Experimental Committee and complied with the principles of laboratory animal care. Animals were housed individually in a climate-controlled animal care facility with a constant room temperature and humidity. All animals had free access to food and drinking water. Upon arrival animals were acclimatized for one week and subsequently randomized on basis of bodyweight. The experiments were divided in: A-experiments, designed to test the effect of the individual ingredients and B-experiments, designed to test the effect of the complete mixture of ingredients that resembles the composition according to the invention. In both A- and B-experiments, mice were divided into a control group (C) receiving control diet, a tumour-bearing control group (TB) receiving control diet and tumour-bearing experimental groups (TB-nutritional ingredient). Data shown are derived from the combination of several experimental runs with identical animal characteristics and experimental procedures (unless stated otherwise).

The tumour-bearing experimental group in the A-experiments received a diet based on AIN93-M (Research Diet Services, Wijk bij Duurstede, the Netherlands) with either fish oil comprising ω-3 polyunsaturated fatty acids selected from the group of eicosapentaenoic acid, docosahexaenoic acid, eicosatetraenoic acid and docosapentaenoic acid (TB-FO), specific oligosaccharide mixture as immune modulator (TB-SOM) or high protein enriched with leucine (TB-HPrleu) supplied as pellets and in the B-experiments a diet with the combination of fish oil, specific oligosaccharide mixture and high protein/leucine (TB-SNC). The latter diet differed in macronutrient composition from AIN93-M to achieve a more humanized diet supplied as dough for product technical reasons.

The control diet in the A-experiments contained per kg food: 126 g protein (100 wt % casein), 727 g carbohydrates and 40 g fat (100 wt % soy oil). The experimental diets in the A-experiments were adapted by adding 22.1 g fish oil (providing 6.9 g EPA and 3.1 g DHA) per kg food (TB-FO), 18 g short chain galacto-oligosaccharides (Vivinal GOS, Friesland Domo Foods, Zwolle, The Netherlands) and 2 g short chain fructo-oligosaccharides (Beneo p95, Orafti, Wijchen, The Netherlands) per kg food (TB-SOM) or 151 g casein/kg and 16 g leucine/kg food (TB-HPrleu).

The control diet in the B-experiment contained more fat and a more Western type of fat blend, although the diet is isocaloric and isonitrogenous compared to the control diet in experiments A, per kg food: 126 g protein (100 wt % casein), 699 g carbohydrates and 52.6 g fat (100 wt % corn oil). This control diet did not demonstrate any effect on immune parameters in the used animal model (data not shown). The experimental diet in experiment B contained per kg food: 210 g protein (189 g intact protein of which 68 w % casein and 32 w % whey and 21 g free leucine), 561 g carbohydrates, 52.5 g fat (20.2 g corn oil, 10.2 g canola oil and 22.1 g fish oil (providing 6.9 g EPA and 3.1 g DHA), 18 g short chain galacto-oligosaccharides and 2 g short chain fructo-oligosaccharides.

Experimental Design.

Murine colon-26 adenocarcinoma cells were used to induce cachexia in mice. Shortly, on day 0 tumour cells ($5 \times 10^5$ cells in 0.2 ml) were inoculated, under general anesthesia (isoflurane/$N_2O/O_2$), subcutaneously into the right inguinal flank of CD2F1 mice in the tumour-bearing groups. Animals in the control group received a sham injection with 0.2 ml HBSS. Body weight (BW), food intake and tumour size (length and width) were measured three times a week. To investigate effects on the immune system contact hypersensitivity (CHS) against oxazolone was determined, as an in vivo model for cellular (Th1 dependent) immunity. Briefly, on day 8 all animals were sensitized with 150 µl 3% oxazolone solution (4-Ethoxymethylene-2-phenyl-2-oxazolin-5-one, Sigma-Aldrich Chemie, Zwijndrecht, The Netherlands, 300 mg in 7.5 ml 96% ethanol and 2.5 ml acetone) applied on their shaved breast and abdomen. Subsequently, at day 13, ear thickness was measured under general anesthesia and all animals were hapten challenged with 25 µl 0.8% oxazolone solution (32 mg in 3 ml 96% ethanol and 1 ml acetone) topical to the ear pinnae. At day 14 after tumour inoculation (24 hours after the challenge), ear swelling was measured under general anesthesia to determine the Th1 immune response.

At day 20, blood was collected by cardiac puncture and sampled in heparin tubes. After sacrification, spleens were dissected, weighed and stored in cold culture medium (RPMI-1640 containing 25 mM HEPES and 2 mM L-glutamine, Life-Technologies, Merelbeke, Belgium, enriched with 100 U/ml penicillin/streptomycin) with 10% heat-inactivated fetal calf serum ($FCS^{hi}$) for immunological analysis. Skeletal muscles (m. Tibialis Anterior (mTA), m. Extensor Digitorum Longus (mEDL), m. Soleus (mS) and m. Gastrocnemius (mG)), tumour, epididymus fat, thymus, were dissected, weighted and frozen at −80° C. (skeletal muscles).

Results

Physiological Cachexia and Immune Parameters

At day 20 after tumour inoculation mice were sacrificed and both cachexia and immune parameters were measured. Data from the different experiments with the individual nutritional ingredients or combinations (A-experiments) were combined and displayed in Table 1 and data from the experiment to test the efficacy of the complete mixture of FO, SOM and high protein/leucine (B-experiment) were presented in Table 2. In experiments A, bodyweight (BW) and carcass weight (CW=BW minus tumour weight (TW)) were significantly decreased from 24.4 gram (both) in the control (C) group to 22.8 and 20.7 gram respectively in the tumour bearing control (TB) group, while in experiment B a decrease was observed from 25.7 gram (both) in the C group to 20.1 and 18.0 gram respectively in the TB group. This reduction could be caused by the significant weight loss of fat and skeletal muscles in the TB group. Food intake has been controlled and was not affected in both experiments A and B (unpublished data).

Addition of one of the individual nutritional ingredients to the diet did not result in any significant effect on BW or CW compared with animals in the TB group. However, a diet containing the complete mixture of FO, SOM and high protein/leucine improved both BW and CW significantly from 20.1 and 18.0 gram respectively in the TB group to 21.9 and 20.3 gram respectively in the TB-SNC group (Table 2), indicating a less cachectic state of the mice. This was emphasized by a positive effect on other cachectic features such as a significant inhibition of weight loss of epididymus fat and skeletal muscles, which was absent after feeding a diet with the individual nutritional ingredients. However, weight loss of both epididymus fat and the skeletal muscle mTA was already decreased significantly after the addition of the combination of FO and high protein/leucine (unpublished data).

In both experiments A and B thymus weight was significantly decreased after tumour inoculation with 47.9% and 61.7% respectively, whereas spleen weight was more than twice as high in the TB group compared to the C group. After the addition of FO or the complete mixture of FO, SOM and high protein/leucine to the diet, a significant inhibition of thymus weight loss was observed, while none of the individual nutritional ingredients affected spleen weight (Table 2).

Table 1 shows the effect of oral administration of fish oil, specific oligosaccharide mixture or high protein/leucine on physiological cachexia parameters and immune parameters in tumour-bearing mice. Data from different experiments were combined and represent means±SEM of control (C) group (n=40), tumour-bearing control (TB) group (n=40) and tumour-bearing groups after supplementation with fish oil (TB-FO, n=10), specific oligosaccharide mixture (TB-SOM, n=10) or high protein/leucine (TB-HPrleu, n=10). * Significant different (p<0.0125) from tumour bearing control group (TB).

Table 2 shows the effects of oral administration of the complete mixture of fish oil, specific oligosaccharide mixture and high protein/leucine on physiological cachexia parameters and immune parameters in tumour-bearing mice.

Data represent means±SEM of control (C) group (n=10), tumour-bearing control (TB) group (n=19) and tumour-bearing group after oral administration of the specific nutritional composition (TB-SNC) (n=20). * Significant different (p<0.025) from tumour bearing control group (TB). $^a$ defined as $GR-1^{high}$ cells, $^b$ defined on the base of forward- and side-scatter profile, $F4/80^{dull}$ and $GR-1^{low\ to\ dull}$, $^c$ defined as $F4/80^{high}$ cells.

TABLE 1

| Cachexia | C | TB | TB-FO | TB-SOM | TB-HPrleu |
|---|---|---|---|---|---|
| Body weight (g) | 24.4 ± 0.3* | 22.8 ± 0.4 | 23.0 ± 0.8 | 23.8 ± 0.8 | 21.8 ± 0.6 |
| Tumour weight | 0.0 ± 0.0* | 2.2 ± 0.1 | 2.1 ± 0.1 | 2.2 ± 0.1 | 1.8 ± 0.1 |
| Carcass weight | 24.4 ± 0.3* | 20.7 ± 0.4 | 20.9 ± 0.8 | 21.5 ± 0.8 | 20.0 ± 0.6 |

TABLE 1-continued

| Cachexia | C | TB | TB-FO | TB-SOM | TB-HPrleu |
|---|---|---|---|---|---|
| Immune | C | TB | TB-FO | TB-SOM | TB-HPrleu |
| Thymus weight | 35.9 ± 1.2* | 18.7 ± 1.0 | 21.1 ± 2.1* | 20.2 ± 2.1 | 14.5 ± 1.8 |
| Spleen weight | 98.7 ± 2.9* | 267.7 ± 8.1 | 231.1 ± 9.8 | 284.1 ± 20.5 | 232.9 ± 15.8 |

TABLE 2

| Cachexia | C | TB | TB-SNC |
|---|---|---|---|
| Body weight (g) | 25.7 ± 0.5* | 20.1 ± 0.4 | 21.9 ± 0.5* |
| Tumour weight (g) | 0.0 ± 0.0 | 2.1 ± 0.1 | 1.8 ± 0.1* |
| Carcass weight (g) | 25.7 ± 0.5* | 18.0 ± 0.3 | 20.3 ± 0.5* |
| Epididymus fat (mg) | 230.3 ± 17.4* | 40.9 ± 10.9 | 88.2 ± 10.9* |
| m. Tibialis Anterior (mg) | 44.7 ± 1.0* | 33.6 ± 0.7 | 38.5 ± 0.8* |
| m. EDL (mg) | 8.9 ± 0.2* | 6.7 ± 0.2 | 7.6 ± 0.2* |
| m. Soleus (mg) | 6.4 ± 0.2* | 4.8 ± 0.1 | 5.4 ± 0.2* |
| m. Gastrocnemius (mg) | 132.1 ± 2.4* | 99.5 ± 2.2 | 110.7 ± 2.9* |
| Immune | C | TB | TB-SNC |
| Thymus weight (mg) | 36.8 ± 1.8* | 14.1 ± 1.1 | 20.7 ± 1.8* |
| Spleen weight (mg) | 95.2 ± 4.3* | 210.5 ± 14.3 | 209.8 ± 9.3 |
| Spleen cells | 2.7 ± 0.1* | 5.6 ± 0.5 | 5.6 ± 0.3 |
| Granulocytes$^a$ (%) | 4.6 ± 0.6* | 28.2 ± 1.9 | 28.2 ± 1.4 |
| Granulocytes$^a$ | 50.8 ± 7.8* | 598.9 ± 44.1 | 613.4 ± 29.2 |
| Monocytes$^b$ (%) | 2.7 ± 0.2* | 5.8 ± 0.2 | 6.2 ± 0.3 |
| Monocytes$^b$ | 29.1 ± 2.2* | 126.0 ± 8.3 | 139.6 ± 11.0 |
| Macrophages$^c$ (%) | 5.0 ± 0.2 | 5.0 ± 0.3 | 4.0 ± 0.2* |
| Marophages$^c$ | 54.9 ± 4.2* | 110.7 ± 10.9 | 87.3 ± 5.2 |
| CD3 + CD4 + T-cells | 6.9 ± 0.4* | 3.6 ± 0.2 | 4.2 ± 0.3 |
| CD3 + CD4 + T-cells | 75.7 ± 5.8 | 78.7 ± 6.3 | 90.8 ± 6.2 |
| CD3 + CD8 + T-cells | 3.2 ± 0.2* | 1.7 ± 0.1 | 1.7 ± 0.1 |
| CD3 + CD8 + T-cells (cells/spleen) | 35.4 ± 3.2 | 34.8 ± 2.0 | 36.9 ± 2.6 |

Contact Hypersensitivity

A contact hypersensitivity (CHS) test was performed at day 13/14 to determine in vivo immune function prior to weight loss. CHS responses were significantly reduced in the TB group compared to the C group in experiments A (28.1%, FIG. 1) and B (31.0%, FIG. 2) indicating an impaired Th1 immune response in tumour bearing mice. After adding one of the individual nutritional ingredients to the diet of tumour-bearing mice no effect was observed on this immune biomarker (FIG. 1). However, after administration of the complete mixture of FO, SOM and high protein/leucine to the tumour-bearing mice (TB-SNC), immune responsiveness was increased significantly by 20.7% compared to the TB mice, demonstrating a better Th1 mediated immune response (FIG. 2).

FIG. 1 shows the effects of oral administration of fish oil, specific oligosaccharide mixture or high protein/leucine on contact hypersensitivity in tumour-bearing mice. Data represent means (µm)±SEM of control (C) group (n=20), tumour-bearing control (TB) group (n=20) and tumour-bearing groups after supplementation with fish oil (TB-FO, n=10), specific oligosaccharide mixture (TB-SOM, n=10) or high protein/leucine (TB-HPrleu, n=10). * Significant different (p<0.0125) from tumour bearing control group (TB).

Figure 2:
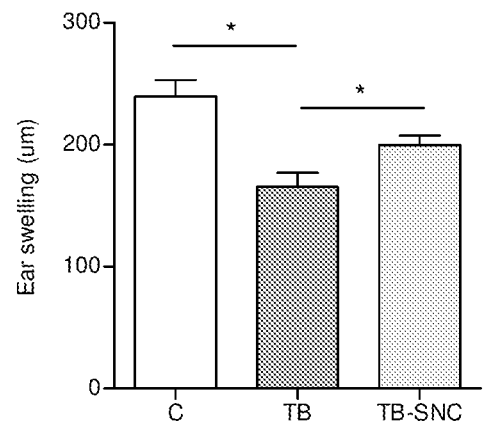
FIG. 2 is a graph of the effects of oral administration of the complete mixture of fish oil, specific oligosaccharide mixture and high protein/leucine on contact hypersensitivity.

FIG. 2 shows the effects of oral administration of the complete mixture of fish oil, specific oligosaccharide mixture and high protein/leucine on contact hypersensitivity Data represent means±SEM of control (C) group (n=10), tumour-bearing control (TB) group (n=19) and tumour-bearing group after oral administration of the specific nutritional composition (TB-SNC) (n=20). *Significant different (p<0.025) from tumour bearing control group (TB).

Example 2

Figure 3:
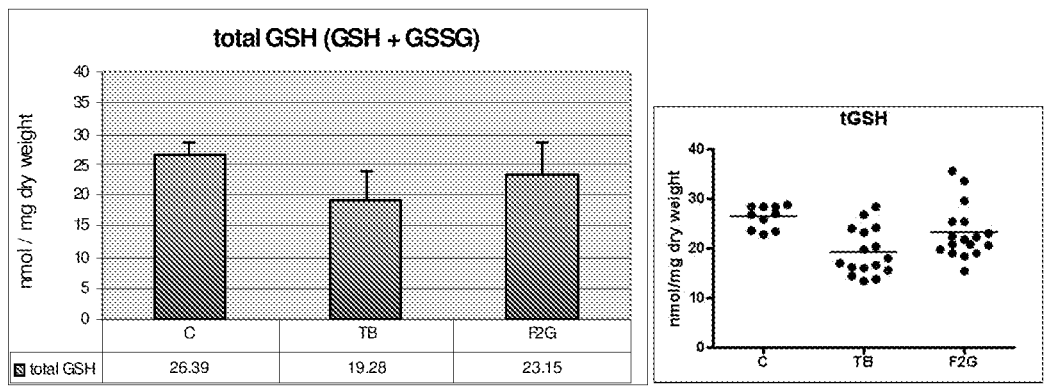
FIG. 3 is a graph of total liver GSH of a control group (C), tumour bearing group (TB) and a nutritional combination group (F2G).
Figure 4:
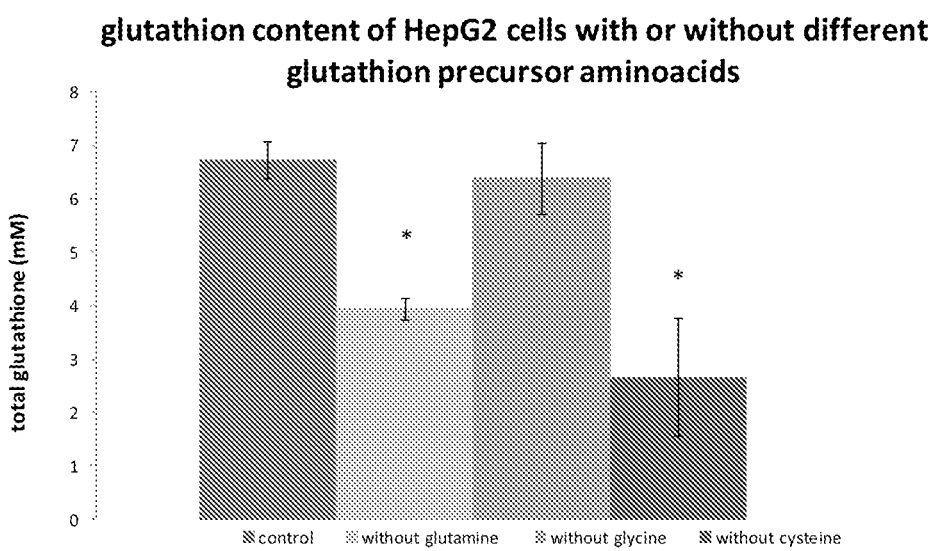
FIG. 4 is a graph of glutathione content of HepG2 cells with or without different glutathione precursor aminoacids.

In cancer cachectic mice, it was shown that the glutathione levels of the liver were decreased (FIG. 3). FIG. 3 shows total liver GSH of control group (C), tumour bearing group (TB) and a nutritional combination group (F2G) that received a diet with the same composition as the TB-SNC group in Example 1. Results are plotted in the left part of the figure as average+std (nmol/mg dry weight)) and as a dot plot in the right part of the figure. For the tumour bearing group (TB) vs control group: p=0.001. For the nutritional combination group (F2G) vs the tumour bearing group: p=0.042. Statistical Tests were done with Mann-Whitney. In experiments using an in vitro model of normal liver, it was demonstrated that glutamine and cysteine have a positive effect on the glutathione homeostasis in liver HepG2 cells (FIG. 4). It was further demonstrated, that a nutritional combination rich in glutamine and cysteine, containing whey (rich in cysteine) and casein (rich in glutamine), fish oil and leucine administrated to tumour-bearing mice resulted in partial normalization of the glutathione content of the liver (FIG. 4).

Example 3

In this experiment the effects of oral administration of a combination of nutritional ingredients were investigated on *Pseudomonas aeruginosa* infection in C3H/HeN mice receiving chemotherapy.

Materials and Methods

Female C3H/HeN mice (Charles River, the Netherlands) were 7-8 weeks of age at the start of the experiment. The animals were housed in individually ventilated cages (IVC) and all animal handling was performed in a laminar flow cabinet. The housing featured a 12:12 dark-light cycle with a constant room temperature of 21°±2 C, humidity 50±5%. Animals were acclimatized upon arrival for one week.

The animals received diets C and FC-2G with the same composition as the control diet (C; n=18) and supplemented TB-SNC diet (FC-2G; n=18) in experiment B of example 1. In addition, a group of animals received diet C but did not receive chemotherapy (group CT-C; n=8), to show that infection does not occur without chemotherapy.

*Pseudomonas aeruginosa* strain PAO-1 (ATTC BAA-47) was subcultered on Nutrient Agar and innoculated into Trypticase Soy Broth (500 ml). The overnight culture was washed, concentrated and diluted to a concentration of ca. $1 \times 10^9$ CFU/ml in PBS (D-PBS, Invitrogen)+3% bicarbonate (for neutralization of gastric acid) as determined by spectrophotometry ($OD_{600} \approx 1 \times 10^9$ cfu/ml).

The number of bacteria was confirmed by plating dilutions (in PBS) of bacteria on *Pseudomonas* C—N selective supplement agar (Oxoid CM0559+SR0102E).

Experiment Setup and Timelines

Stage 1: Before infection with PAO1, the mice were pre-treated with the broad-spectrum antibiotic Ampicillin, (i.p. injection, 200 mg/kg solved in 0.2 ml saline, Sigma) for three consecutive days to obtain selective intestinal tract decontamination (day −2, −1 and 0).

Stage 2: The mice in were infected with 0.2 ml ampicillin resistant *Pseudomonas aeruginosa* (PAO-1 strain ATTC BAA-47: $10^9$ cfu/ml in PBS+3% bicarbonate) administered by oral gavage (infection on day 0).

Stage 3: On day six the mice were matched within the different groups on PAO1 colonization level as measured in fresh feces and on their body weight so that at the beginning of the dietary intervention each group had the same weight and PAO1 colonization distribution. After the animals were matched the dietary intervention is started. Control groups C and CT-C received diet C, group FC-2G received the supplemented FC-2G diet.

Stage 4: After 3 weeks of dietary intervention (Day 28) a chemotherapeutic agent was administered, resulting in neutropenia and reduced immune function. On day 28 and day 30, the mice received 100 mg cyclophosphamide per kilogram of body weight i.p. A chemotherapy-control group (CT-C; n=10) received an i.p. injection with physiological salt solution on these days.

Stage 5: The mice were sacrificed 5 days after the chemotherapy started. Liver was removed aseptically to determine bacterial translocation, a parameter for systemic bacterial infection with PAO1.

Aseptically removed liver was collected in 0.5 ml BPW, weighed, put on ice and homogenized by using an ultraturrax (IKA, autoclavable disposable turrax). Ten-fold dilution series were made in PBS and plated on Nutrient Agar and C—N agar plates. After overnight incubation at 37° C. the number of specific *Pseudomonas aeruginosa* were determined.

Statistical significance of differences between the C and FC-2G groups were tested by Student's T-test for the number of translocated bacteria and using Pearson Chi-square analysis for the incidence of translocation.

Results

Data are shown in Table 3. Mice that did not receive chemotherapy did not show any PAO1 translocation in the liver (group CT-C). In mouse that received chemotherapy, the incidence of measurable PAO1 translocation as well as the average number of translocated bacteria per mouse was significantly lower in the group that received the supplemented diet (group FC-2G) versus the control diet (group C). The results indicate that supplementation with the FC-2G diet reduces chemotherapy-induced bacterial infection.

Hence, in an embodiment of the invention, the composition according to the invention is suitable for the treatment of neutropenia, in particular chemotherapy-induced neutropenia.

TABLE 3

Bacterial translocation of *Pseudomonas aeruginosa* in mice receiving chemotherapy

| | Group | | | Statistics p-value C vs. FC-2G |
|---|---|---|---|---|
| | CT-C | C | FC-2G | |
| Incidence of translocation | 0% | 94.40% | 61.10% | <0.05 |
| Average CFU/liver ($^{-2}$log CFU ± SEM) | n.d. | 4.80 ± 0.52 | 2.74 ± 0.61 | <0.05 |
| Animals per group (n) | 8 | 10 | 18 | | n.d. = not detectable

Example 4

The following composition (Table 4) was made according to standard procedures and is suitable for use according to the invention, preferably as a sip feed.

TABLE 4

Main ingredients of composition according to the invention

| INGREDIENTS | AMOUNT |
|---|---|
| Energy content | 160 kcal/100 ml |
| Protein (26.9 en %) | 10.1 g/100 ml of which: |
| | whey : 2.92 g/100 ml |
| | casein : 6.06 g/100 ml |
| | added leucine: 1.10 g/100 ml |
| | wherein the following amino acids are present (based on total protein weight): |
| | L-Leucine: 19.4 wt % |
| | L-Glutamine/Glutamic acid: 17.8 wt % |
| | L- Cysteine: 0.9 wt % |
| | Lysine: 7.5 wt % |
| | leu/(val + ile) – ratio = 1.83 |
| Carbohydrates (43.6 en %) | 17.4 g/100 ml of which: |
| | sugar blend comprising glucose, galactose, lactose, maltose, sucrose and trehalose (12.7 g/100 ml) |
| | starch (4.3 g/100 ml) |
| Lipids (29.8 en %) | 5.3 g/100 ml of which: |
| | ω – 3 |
| | ALA (1.8 g/100 g of total lipid) |
| | EPA (11.9 g/100 g of total lipid) |
| | DHA (5.8 g/100 g of total lipid) |
| | DPA (1.4 g/100 g of total lipid) |
| | SDA (1.8 g/100 g of total lipid) |
| | ω – 6 |
| | LA (26.0 g/100 g of total lipid) |
| | AA (0.7 g/100 g of total lipid) |
| | ω – 3/ω – 6 = 0.87 |
| Dietary fibre | 2 g/100 ml of galactooligosaccharides |
| Minerals, Trace elements, Vitamines, Taurine and Carnitine | |
| Viscosity | 41 mPa · s |

Example 5

Objective

To investigate the effects of short term nutritional supplementation on lipopolysaccharide (LPS)-stimulated cytokine and prostaglandin production in whole blood of healthy volunteers.

Design

A single-arm, open-label design was used for this exploratory study. Twelve healthy volunteers were included after obtaining written informed consent. In the morning of Visit 1, subjects consumed the basic sip feed (200 ml) to standardize baseline values. For one week, the subjects consumed 2×200 ml Test sip feed daily. The composition contained 27 en % proteinaceaous matter, 19 wt. % total leucine, 890 mg per 100 ml of EPA+DHA, and GOS+FOS as immunomodulating oligosaccharides (for detailed composition, see Table 5). Blood was collected at day 1, 2, 3, 5 and 8. Ex vivo pro-inflammatory cytokine and Prostaglandin $E_2$ ($PGE_2$) production in Lipopolysaccharide (LPS)-stimulated whole blood was measured.

Composition

The composition of the Test sip feed was as given in Table 5:

TABLE 5

|  |  | SIP FEED | | |
|---|---|---|---|---|
|  |  | label claim 100 ml | packaging unit 200 ml | daily dose 400 ml |
| Energy |  | kcal | 160.0 | 320.0 | 640.0 |
| Protein |  | E % | 26.9 | | |
|  |  | g | 10.10 | 20.20 | 40.40 |
|  | Casein | g | 6.06 | 12.12 | 24.24 |
|  | Whey | g | 2.92 | 5.84 | 11.68 |
|  | Leucine (free amino acid) | g | 1.10 | 2.20 | 4.40 |
| Carbohydrate |  | E %* | 43.5 | | |
|  |  | g | 17.4 | 34.80 | 69.60 |
|  | Sucrose | g | 3.92 | 7.84 | 15.68 |
|  | Maltodextrin | g | 7.84 | 15.68 | 31.36 |
|  | Trehalose | g | 3.92 | 7.84 | 15.68 |
|  | Lactose | g | 0.70 | 1.40 | 2.80 |
| Fat |  | E % | 29.8 | | |
|  |  | g | 5.3 | 10.60 | 21.20 |
|  | Saturated fatty acids | g | 0.76 | 1.52 | 3.04 |
|  | Monounsaturated fatty acids | g | 1.48 | 2.96 | 5.92 |
|  | Polyunsaturated fatty acids | g | 2.52 | 5.04 | 10.08 |
|  | EPA (from fish oil) | g | 0.597 | 1.19 | 2.39 |
|  | DHA (from fish oil) | g | 0.292 | 0.58 | 1.17 |
| Fiber |  | g | 2.00 | 4.00 | 8.00 |
|  | fructooligosaccharides (FOS) | g | 0.20 | 0.40 | 0.80 |
|  | transgalactooligosaccharides (GOS) | g | 1.80 | 3.60 | 7.20 |
| Minerals |  |  |  |  |  |
|  | Sodium | mg | 110 | 220 | 440 |
|  | Potassium | mg | 215 | 430 | 860 |
|  | Chloride | mg | 140 | 280 | 560 |
|  | Calcium | mg | 141 | 282 | 564 |
|  | Phosphorus | mg | 115 | 230 | 460 |
|  | Magnesium | mg | 28.2 | 56 | 113 |
| Trace Elements |  |  |  |  |  |
|  | Iron | mg | 1.90 | 3.80 | 7.60 |
|  | Zinc | mg | 2.05 | 4.10 | 8.20 |
|  | Copper | mcg | 288.0 | 576.0 | 1152.0 |
|  | Manganese | mg | 0.68 | 1.36 | 2.72 |
|  | Fluoride | mg | 0.16 | 0.32 | 0.64 |
|  | Molybdenum | mcg | 16.0 | 32.0 | 64.0 |
|  | Selenium | mcg | 13.5 | 27.0 | 54.0 |
|  | Chromium | mcg | 11.0 | 22.0 | 44.0 |
|  | Iodine | mcg | 21.0 | 42.0 | 84.0 |
| Vitamins |  |  |  |  |  |
|  | Vitamin A | mcg RE | 130.0 | 260.0 | 520.0 |
|  | carotenoids | mg | 0.3 | 0.6 | 1.3 |
|  | Vitamin D | mcg | 1.10 | 2.2 | 4.4 |
|  | Vitamin E | mg α-TE | 3.20 | 6.4 | 12.8 |
|  | Vitamin K | mcg | 8.50 | 17.0 | 34.0 |
|  | Vitamin B1 (Thiamine) | mg | 0.24 | 0.5 | 1.0 |
|  | Vitamin B2 (Riboflavin) | mg | 0.25 | 0.5 | 1.0 |
|  | Niacin | mg NE | 2.90 | 5.8 | 11.6 |
|  | Pantothenic Acid | mg | 0.85 | 1.7 | 3.4 |
|  | Vitamin $B_6$ | mg | 0.58 | 1.2 | 2.3 |
|  | Folic Acid | mcg | 53.0 | 106.0 | 212.0 |
|  | Vitamin $B_{12}$ | mcg | 0.64 | 1.3 | 2.6 |
|  | Biotin | mcg | 6.40 | 12.8 | 25.6 |
|  | Vitamin C | mg | 21.0 | 42.0 | 84.0 |
|  | Choline | mg | 59.0 | 118.0 | 236.0 |
| Extra additions |  |  |  |  |  |
|  | Taurine | mg | 13.0 | 26.0 | 52.0 |
|  | Carnitine | mg | 11.0 | 22.0 | 44.0 |

*including organic acids and polyols

Results

Twelve subjects (mean±SD for age: 62.0±4.8 years and BMI of 25.6±3.2 kg/m$^2$) participated in the study. After one week of nutritional supplementation, ex vivo cytokine production of IL-1β, IL-6, IL-8, IFN-γ and TNF-α in LPS-stimulated whole blood showed an increase, as shown in Table 6.

TABLE 6

Ex vivo LPS-stimulated cytokines and PGE$_2$ production in whole blood
(LPS concentration 100 – 0 ng/ml), ITT population (n = 12).

| Cytokines & PGE$_2$ in pg/ml | Baseline Day 1 | Day 3 | Day 5 | Day 8 | Day 8 minus Day 1 |
|---|---|---|---|---|---|
| IL-1β | 540 | 699 | 1141$^A$ | 1065 | 473 |
|  | (370-786) | (495-920) | (883-1513) | (699-1468) | (210-910) |
| IL-6 | 18237 | 18817 | 23166 | 23494$^A$ | 7095 |
|  | (9646-22270) | (15233-21117) | (17375-27442) | (17030-31796) | (2104-13978) |
| IL-8 | 1608 | 1741 | 2322$^A$ | 2610$^A$ | 620 |
|  | (1447-2139) | (1427-2305) | (1847-2971) | (1864-2772) | (376-817) |
| IFN-γ | 1683 | 2060$^A$ | 2777$^A$ | 2612$^A$ | 1088 |
|  | (1207-1880) | (1732-2480) | (2262-3248) | (2197-3097) | (869-1283) |
| TNF-α | 1642 | 2276 | 3712$^A$ | 3144$^A$ | 1400 |
|  | (1147-2868) | (1742-4213) | (2961-5884) | (2058-4881) | (917-2216) |
| PGE$_2$ | 326 | 277 | 305 | 306 | −60 |
|  | (198-1014) | (−37-1194) | (−60-626) | (57-804) | (−235-106) |

Data are presented as medians (25$^{th}$-75$^{th}$ percentiles)
$^A$Significantly different from baseline
p = 0.008 using the combined Wilcoxon signed rank-test for men and women.

Conclusion

The ex vivo cytokine production of IL-1β, IL-6 IL-8, IFN-γ and TNF-α in LPS-stimulated whole blood increased during the intervention period, which implies an improved immune response against exogenous pathogen-related stimuli after one week of nutritional supplementation in healthy volunteers.

Example 6

Definition

The glycaemic index (GI) of a carbohydrate provides a measure of its ability to raise postprandial glucose concentrations. High GI foods give higher postprandial blood glucose levels than those with a low GI. The GI of a carbohydrate also predicts the insulin response to that food.

The GI of a carbohydrate is calculated by assessing a 25 g two-hourglycaemic response with that of a subsequent 25 g carbohydrate standard glucose:

GI equals 'Incremental area under blood glucose response curve for a test food containing 25 g of carbohydrate' divided by 'Corresponding area after equivalent carbohydrate portion of glucose'

Glycaemic Index Methodology

Available carbohydrate is defined for GI testing purposes as: Total carbohydrate minus the indigestible carbohydrates (soluble and insoluble) that are from a physiological point dietary fibres (e.g. inulin, FOS, type 3 resistant starch).

The samples provided should be representative of the product as available to the consumer in the market place.

All foods submitted for testing are tested in vivo, that is, in 10 human subjects consuming amounts containing the equivalent of 25 g available carbohydrate. They are healthy subjects with no chronic diseases, diabetes or glucose impairment. Subjects have a BMI between 18.5-27 kg/m$^2$.

Reference food: The reference food is 25 g glucose powder dissolved in 250 mls water. Each person tests the reference food at least twice.

Test foods: The test foods are prepared according to manufacturer's instructions, representing the food as normally consumed. The test foods are consumed once only on separate occasions as a portion providing 25 g of available carbohydrate, defined as above.

Protocol Subjects: Subjects are tested in the morning after a 10-12 h overnight fast. Two fasting blood samples are taken (−5 & 0) 5 minutes apart after which subjects consume the test meal or reference food at an even rate over 15 minutes. Further blood samples are taken at 15, 30, 45, 60, 90 and 120 minutes after the beginning of the meal. The test meal and reference food should be consumed with a 250 mls drink of water. This remains constant for each of the tests in the series.

24 hrs prior to GI test: The day before each session, subjects refrain from drinking alcohol and avoid unusual levels of exercise and food intake. Subjects must have an evening meal based on a carbohydrate-rich food, such as rice, pasta, bread, potatoes and not too much fat. This meal should not include beans, pulses or legumes (to avoid a second meal effect the next morning). It is important that they eat dinner and not fast for more than 18 hours. Subjects are asked to be in a similar state each time they come in for a session. After they have eaten their evening meal, subjects fast for at least 10 hours overnight before the start of their test session the next morning. They can drink only water during the fasting period.

Blood sampling: Blood will be obtained by finger pricking.

Blood is collected without clotting inhibitors (heparin, EDTA).

Glucose assay: Whole capillary blood or is measured by an automatic glucose analyzer. In this case, Hemocue glucose analysers are used.

Data analysis: The incremental area under the blood glucose response curve (iAUC), ignoring area beneath the baseline, is calculated geometrically as follows:

For times t0, t1, . . . to the blood glucose concentrations are G0, G1, . . . Gn, respectively:

$$iAUC = \sum_{n}^{x=1} Ax$$

wherein Ax=the AUC for the xth time interval (ie. between tx−1 and tx).

For the first time interval (ie. x=1): if G1>G0, A1=(G1−G0)×(t1−t0)/2 otherwise, A1=0

For the other time intervals (ie. x>1)

if Gx≥G0 and Gx−1≥G0, Ax={[(Gx−G0)/2]+(Gx−1−G0)/2}×(tx−tx−1)

if Gx>G0 and Gx-1<G0, Ax=[(Gx-G0)²/(Gx-Gx-1)]× (tx-tx-1)/2 if Gx<G0 and Gx-1>G0, Ax=[(Gx-1-G0)²/(Gx-1-Gx)]×(tx-tx-1)/2 if Gx≤G0 and Gx-1≤G0, Ax=0

GI calculation: In individual subjects, the GI value is the iAUC for each food expressed as a percentage of the mean iAUC of the two reference foods (glucose). The GI of the test food is the mean GI±SEM of the 10 subjects.

Up to two outliers (an outlier is an individual whose GI differs from the mean by more than two SD) may be excluded from the data set. SEM should be within 20% of the mean.

What is claimed:

1. A method for treating neutropenia in a mammal, comprising administering a nutritional composition to the mammal in need thereof, said nutritional composition comprising:
   (a) 18-50 en % of proteinaceous matter;
   (b) at least 12 wt % of leucine, based on total proteinaceous matter;
   (c) 10-50 en % of lipids, said lipids comprise at least 15 wt % based on total lipid content of a ω-3 polyunsaturated fatty acid selected from eicosapentaenoic acid, docosahexaenoic acid, eicosatetraenoic acid and docosapentaenoic acid;
   (d) 20-50 en % of digestible carbohydrates;
   (e) 1-15 wt % of indigestible galactooligosaccharide and fructooligosaccharide, based on total dry matter, the molar ratio of said galactooligosaccharide and fructooligosaccharide ranges from 1:1 to 20:1, said nutritional composition has an energetic value of between 0.3 kcal/ml and 3.0 kcal/ml if it is provided as a liquid nutritional composition or an energetic value of between 3.2 kcal/g and 8.0 kcal/g if it is provided as a semi-liquid, gel or solid nutritional composition.

2. The method according to claim 1, wherein the mammal has a reduced immune function which manifests itself as a symptom selected from the group consisting of infections, inflammations, vascular complications, bad wound healing, mucositis and stomatitis.

3. The method according to claim 1, wherein the nutritional composition is administered to a mammal suffering from cancer.

4. The method according to claim 1, wherein the mammal has a trauma selected from the group consisting of surgery, drug treatment, chemotherapy and radiotherapy.

5. The method according to claim 1, wherein the nutritional composition is administered to a mammal receiving an anti-cancer immunotherapy or planning to start anti-cancer immunotherapy within a period of two months, and wherein the nutritional composition enhances the effectiveness of an immunotherapy.

6. The method according to claim 1, wherein the nutritional composition is a liquid nutritional composition comprising at least 7 g/100 ml of proteinaceous matter.

7. The method according to claim 1, wherein the proteinaceous matter originates from at least one protein source selected from the group of whey protein, casein, caseinate, soy protein and wheat protein.

8. The method according to claim 1, wherein the proteinaceous matter comprises at least 15 wt. % whey protein.

9. The method according to claim 1, wherein the nutritional composition comprises leucine in the form of a free acid, a salt, a dipeptide or a conjugate with a conjugating compound other than an amino acid, a protein, or a peptide, which conjugate is capable of being split into the free amino acid or salt thereof.

10. The method according to claim 1, comprising between 12 wt. % and 23 wt. % of leucine, based on total proteinaceous matter.

11. The method according to claim 1, comprising between 4 wt. % and 20 wt. % of glutamine, based on total proteinaceous matter.

12. The method according to claim 1, wherein the nutritional composition comprises at least 0.7 wt. % of one or more of the group of cystine, cysteine and cysteine equivalents.

13. The method according to claim 1, wherein the lipid fraction comprises less than 30 wt. % of a saturated fatty acid.

14. The method according to claim 1, wherein the lipid fraction further comprises at least one ω-6 polyunsaturated fatty acid, and wherein the molar ratio of ω-3 polyunsaturated fatty acids to ω-6 polyunsaturated fatty acids is less than 1.0.

15. The method according to claim 1, wherein the nutritional composition further comprises at least one component selected from the group consisting of sodium, potassium, chloride, fluoride, iodide, calcium, phosphorous, magnesium, vitamin A, vitamin D3, vitamin E, vitamin K, vitamin B1, vitamin B2, vitamin B3, vitamin B5, vitamin B6, folic acid, vitamin B12, biotin, vitamin C, lipoic acid, zinc, iron, copper, manganese, molybdenum, selenium and chromium.

16. The method according to claim 1, wherein the mammal is a human.

17. The method according to claim 1, wherein the nutritional composition is administered orally.

18. The method according to claim 1, wherein the nutritional composition is administered enterally.

19. The method according to claim 1, wherein the nutritional composition is administered under supervision of a medical specialist.

20. The method according to claim 16, wherein the nutritional composition is self-administered.

21. The method according to claim 7, wherein the proteinaceous matter originates from at least one protein source selected from the group consisting of whey protein and casein.

22. The method according to claim 1, wherein the nutritional composition comprises a digestible carbohydrate and the nutritional composition has a glycemic index of less than 55.

23. The method according to claim 1, wherein the neutropenia is chemotherapy-induced neutropenia.

24. The method according to claim 1, wherein the indigestible carbohydrate comprises a short chain galactooligosaccharide and a short chain fructooligosaccharide.

* * * * *